United States Patent [19]

Eppstein et al.

[11] Patent Number: 4,522,811

[45] Date of Patent: Jun. 11, 1985

[54] SERIAL INJECTION OF MURAMYLDIPEPTIDES AND LIPOSOMES ENHANCES THE ANTI-INFECTIVE ACTIVITY OF MURAMYLDIPEPTIDES

[75] Inventors: Deborah A. Eppstein; Elizabeth B. Fraser-Smith, both of Los Altos; Thomas R. Matthews, Los Gatos, all of Calif.

[73] Assignee: Syntex (U.S.A.) Inc., Palo Alto, Calif.

[21] Appl. No.: 396,213

[22] Filed: Jul. 8, 1982

[51] Int. Cl.$^3$ ............................................. A61K 37/02
[52] U.S. Cl. ......................................................... 514/2
[58] Field of Search .................. 424/177; 260/112.5 R

[56] References Cited

U.S. PATENT DOCUMENTS

| | | | |
|---|---|---|---|
| 4,082,735 | 4/1978 | Jones et al. | 424/177 |
| 4,186,194 | 1/1980 | Adam et al. | 424/177 |
| 4,224,179 | 9/1980 | Schneider | 424/177 |
| 4,235,771 | 11/1980 | Adam et al. | 424/177 |
| 4,310,505 | 1/1982 | Baldeschwieler et al. | 424/35 |

FOREIGN PATENT DOCUMENTS

| | | |
|---|---|---|
| 0002677 | 7/1979 | European Pat. Off. . |
| 0013651 | 7/1980 | European Pat. Off. . |
| 0021367 | 1/1981 | European Pat. Off. . |

OTHER PUBLICATIONS

Chemical Abstracts, vol. 89, 1978, p. 411, Abst. No. 40710a, Kotani et al.
Jolivet et al., Immunological Communications, 10(6), 511–522 (1981).
Mehta et al., J. of the Reticuloendothelial Society, 32, pp. 155–164 (1982).
Fidler et al., Proc. Natl. Acad. Sci., USA, 78, No. 3, pp. 1680–1684 (1981).

Primary Examiner—Delbert R. Phillips
Assistant Examiner—F. T. Moezie
Attorney, Agent, or Firm—Grant D. Green; Tom M. Moran; Alan M. Krubiner

[57] ABSTRACT

Serial injection of muramyldipeptides and liposomes enhances the anti-infective activity of muramyldipeptides.

9 Claims, No Drawings

SERIAL INJECTION OF MURAMYLDIPEPTIDES AND LIPOSOMES ENHANCES THE ANTI-INFECTIVE ACTIVITY OF MURAMYLDIPEPTIDES

BACKGROUND OF THE INVENTION

1. Scope of the Invention

This invention relates to a method for enhancing the anti-infective activity of muramyldipeptides. More specifically the anti-infective activity of muramyldipeptides may be enhanced by the serial administration of these compounds with liposomes.

1. Background of the Invention

In the field of immunology, more than one injection of a vaccine (or bacterin) is frequently required to achieve the immunological response in a host sufficient to ward off an infection. During the development of the vaccine art it was discovered that substances could be added to the vaccine composition which would enhance the antigenicity of the vaccine to give a superior immune response over that achieved with injection of the vaccine alone. Among the most effective adjuvants developed early on in the vaccine art was Freund's complete adjuvant which is a suspension of killed, whole Mycobacterium tuberculosis in mineral oil plus an emulsifier. Also highly effective was Freund's incomplete adjuvant which is a mineral oil plus an emulsifier only. Notwithstanding that these two adjuvants were used as laboratory standards, they were and are not commercially used because Freund's complete adjuvant is derived from a virulent microorganism, *Mycrobacterium tuberculosis*, and both the complete and incomplete forms contain mineral oil, a human carcinogen. Also, in the absence of the microorganism, this adjuvant does not always produce a satisfactorily high immunological enhancement.

Attempts to find the basic unit responsible for enhancing the cellular antigenicity response resulted in the finding that sugar-containing peptides of the cell wall were the immune stimulating component in the bacterial extracts. A detailed study of the chemistry of mycobacterial cell wall resulted in the observation by F. Ellouz, et al, *Biochem Biophys, Res. Comm.* 59, 1317 (1974) that the adjuvant activity could be directly attributable to the bacterial wall peptidoglycan derivatives. The smallest effective molecule was found to be an N-acetylmuramyldipeptide, specifically N-acetyl-muramyl-L-alanyl-D-isoglutamine, prepared by C. Messer, P. Sinay, and A. Adams, *Biochem, Biophys Res. Comm.* 66, 1316 (1975). This compound is now commonly called muramyldipeptide or MDP.

Subsequently a number of muramyldipeptide analogs and derivatives have been prepared by various academic and industrial concerns. The majority of these compounds have, to one degree or another, been demonstrated to be effective adjuvants. In addition, many of these muramyldipeptide analogs and derivatives are, per se, active against infectious organisms such as *Klebsiella pneumoniae*, *Escherichia coli*, *Candida albicans*, *Staphylococcus aureus* and the like. The journal literature on MDP compounds and their immunological activities is extensive. A number of patents have issued on many such compounds and patent applications are pending on others.

The materials responsible for enhancing the anti-infective activity of muramyldipeptides are liposomes. They are microscopic vesicles, generally spherically shaped, formed from one or several concentric layers (lamellae) of lipid molecules having a lipophilic and hydrophilic moiety. Most frequently, liposomes are water insoluble, amphapathic phospholipids which form bilayer structures spontaneously in aqueous solution. Regardless of the overall shape, the bilayers are organized as closed concentric lamella, with an aqueous layer separating each lamella from its neighbor. The lamella of water soluble liposomes comprise at least one bilipid layer, the molecules of this layer being so oriented that the hydrophilic functions are in contact with the aqueous phase. Since the liposomes lamella layers are being separated from each other by a water film, they have a wall-like structure which can be schematically represented, in sections, by molecular composite XY-YX, X representing the hydrophilic portion of the molecule and Y the lipophilic portion. Liposome vesicle size is highly variable and dependent on the method of manufacture thereof; but generally they have a 25 to 30,000 nm diameter and the film between the bilayer of 3 to 10 nm.

In recent years liposomes have attracted widespread interest from a variety researchers for a number of reasons ranging from the purely theoretical physical chemistry point of view to projected applications, particularly in medicine.

The physical chemistry studies have focused on such properties as fluidity, permeability, and molecular organization. These studies are generally motivated by the importance of the lipid bilayer as a structural element of natural membranes. Liposomes, it has been found, can be used to promote cell cell fussion, alter membrane phospholipid and cholesterol content, and transfer water-soluble, normally impermanent molecules into cells.

In clinical drug research, liposomes have been viewed as a pharmaceutical capsule for the possible selective delivery of therapeutic agents such as insulin, enzymes, interferon and other anti-tumor drugs.

Liposome-encapsulated muramyldipeptide, the native compound, has been used in studies wherein non-cytotoxic macrophages have been rendered tumoricidal by the interaction of macrophage-activating factor and free or encapsulated MDP in studies reported by S. Sone and I. J. Fidler, *The Journal of Immunology*, vol. 125, number 6, pp. 2454–2460 (1980). Two subsequent papers which describe continued studies in this area by are Sone and Fidler (*Cellular Immunology*, 57, 42–50 (1981)) and I. J. Fidler, et al (*Proc. Natl. Acad. Sci. USA*, 78, 1680–1684 (1981)). The in vivo studies of Fidler, et al reported in PNAS indicate that empty multi-lameler vesicles plus free MDP did not activate tumoricidal activity in mice alveolar macrophages when free MDP was administered at the same level as that adequate to cause activation by liposome-encapsulated MDP. These investigators found that a dose of MDP 80 times greater than the liposome encapsulated MDP dose did not activate the tumoricidal activity of mice alveolar macrophages.

It has been shown that the dose of an MDP derivative required for efficacy in protecting mice from bacterial or yeast infections can be reduced significantly by encapsulating the analog in liposomes. For example, to achieve protection against *Candida albicans* yeast infection in mice, the MDP derivative dose was reduced by approximately 15-fold by its encapsulation with multilamellar liposome vesicles, efficacy being also related to the liposome composition. This increased efficacy was only achieved when the liposome-encapsulated drug was given by intravenous injection, which allowed the liposomes to be targeted to the phagocytic cells of the reticuloendothelial system. (See E. B. Fraser-Smith, et al, ASM meeting, March 1982.)

However, it has now been determined that this same increased efficacy can also be achieved without actual encapsulation of the drug in liposomes, or without other types of physical association of the drug with liposomes (such as association with the lipid bilayers) but by simply co-administering the MDP analog with liposomes. The drug can either be mixed with the preformed liposomes prior to injection, or the drug can be injected first followed by injection of the liposomes or liposomes can be injected first, followed by injection of the drug. Such serial administration of liposomes and free MDP compound provides essentially the same protective activity as obtained with the same dose of liposome-encapsulated MDP compound whereas the MDP compound alone was ineffective at a similar concentration and was not found to impart protective activity on an equivalent basis until the dose was increased by at least an order of magnitude.

Therefore, the central aspect of this invention relates to a novel method for enhancing the anti-infective activity of native muramyldipeptide or its analogs and derivatives by serial injection of such compound with liposomes.

SUMMARY OF THE INVENTION

The primary aspect of this invention is a method for enhancing the anti-infective activity of muramyldipeptides which method comprises serial intravenous injection of an unencapsulated muramyldipeptide (MDP) compound and liposomes. This method has utility for any muramyldipeptide type compound and can be carried out in combination with any liposomes prepared from pharmaceutically acceptable material regardless of physical type or size.

The word "enhancing" or "enhancement" as used herein means that for a given anti-infective response in a subject, less MDP material will be needed to effectuate that response than if the MDP compound was administered free, i.e., not in conjunction with liposome material. For the purposes of this invention there is no set percentage figure suggested as a bench mark for what constitutes "enhancement" of anti-infective activity because such enhancement will vary with such factors as: (1) the timing of liposome and MDP administration; (2) MDP efficacy; (3) the physical form and chemical composition of the liposome used; or (4) the liposome concentration, to name some of the factors which will influence drug effectiveness with the method. It has been found that, in essence, the effective amount of MDP, when serially administered with liposomes, is approximately equal to that amount of liposome-encapsulated MDP necessary to elicit the same and/or a similar anti-infective response.

This method has utility for the full spectrum of situations and circumstances where muramyldipeptides have anti-infective utility. As used herein, "anti-infective" activity refers to the ability of the subject to withstand and combat invasion and multiplication of microorganisms in body tissues resulting in local cellular injury due to competitive metabolism, toxins, intracellular replication, or antigen-antibody response. The immunological response may be transient or prolonged, and consists of a cellular response (delayed hypersensitivity) or the production of specific (immunoglobulin) antibodies to the components of the infecting organism or its toxins. That is the ability of an organism to withstand or fend off an infection by bacteria, yeast, fungi, protozoa, molds, actinomycetes, and the like.

The effectiveness of this method in enhancing the anti-infective activity of MDP compounds is shown by treatment of a test animal such as mice with liposomes and an MDP compound, waiting for an appropriate time to allow cellular response to be effected, and then challenging the subjects with an intravenous injection of a usually lethal dose of bacteria, yeast, or the like. Survival time is then used as a measure of efficacy.

For the purpose of this invention, the phrase "MDP compound" refers to all peptidoglycans capable of enhancing the cellular antigenicity response in mammals and being the muramyl dipeptide, N-acetylmuramyl-L-alanyl-D-isoglutamine, or analogs or derivatives thereof. This compound and the known active derivatives and analogs thereof may be represented by the following formula

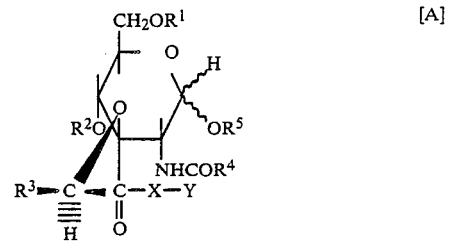

wherein: "$R^1$ and $R^2$ are the same or different and are hydrogen or an acylradical containing from 1 to 22 carbon atoms. $R^3$ is hydrogen or lower alkyl; $R^4$ is an unsubstituted or substituted alkyl radical containing from 1 to 21 carbon atoms, or an unsubstituted or substituted aryl radical containing from 6 to 10 carbon atoms; $R^5$ is hydrogen."

X is an aminoacyl moiety selected from the group consisting of

| | |
|---|---|
| L-alanyl, | L-tryptophanyl, |
| L-valyl, | L-lysyl, |
| l-leucyl, | L-ornithyl, |
| L-isoleucyl, | L-arginyl, |
| L-α-aminobutyryl, | L-histidyl, |
| L-seryl, | L-glutamyl, |
| L-threonyl, | L-glutaminyl, |
| L-methionyl, | L-aspartyl, |
| L-cysteinyl, | L-asparaginyl, |
| L-phenylalanyl, | L-prolyl, and |
| L-tyrosyl, | L-hydroxyprolyl; and |

Y is D-glutamic or D-aspartic acid, or a mono-, di-, or mixed alkyl ester, amide, or lower alkyl amide thereof;

the wavy lines represent the alpha and beta configuration or mixtures thereof wherein if one line in in the alpha position the other is beta; and the pharmaceutically acceptable salts thereof.

As used herein:

"mixed", is meant, for example, the case wherein one carboxyl is in the form of the amide, and the other, the ester;

"alkyl" means a saturated branched or unbranched hydrocarbon chain containing 1–22 carbon atoms;

"lower alkyl" means a branched or unbranched saturated hydrocarbon chain containing 1–4 carbon atoms;

"acyl" means RC- where "R" is alkyl as herein defined;

"aryl" means phenyl or phenyl lower alkyl, e.g. benzyl;

"substituted" means the presence of —OH, —OR$^6$,

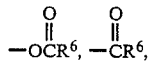

—NH$_2$, —NHR$^6$, or —N(R$^6$)$_2$ wherein "R$^6$" is lower alkyl as herein defined; and "aminoacyl" refers to an alpha-amino acid containing less than 12 carbon atoms.

The wavy lines represent the alpha or beta configuration or mixtures thereof; if one wavy line is alpha the other is beta.

More preferred are those compounds of Formula (I) wherein X is selected from the group consisting of L-valyl, L-alanyl, L-threonyl, L-seryl, L-alpha-aminobutyryl and Y is D-isoglutamine. In addition a preferred embodiment is that wherein R$^6$ is hydrogen, R$^2$ is acetyl, X is L-alanyl and Y is D-isoglutamine.

Most preferred are the compounds:
N-acetylmuramyl-L-alanyl-D-isoglutamine;
N-acetyldesmuramyl-L-alanyl-D-isoglutamine;
N-acetylmuramyl-L-alpha-aminobutyryl-D-isoglutamine; and
N-acetyldesmuramyl-L-alpha-aminobutyryl-D-isoglutamine.

Such compounds are known and described in the periodical and patent literature. For example, Belgian Nos. 834,753; 834,754; 847,103; 849,214; German Nos. 2,710,455; 2,922,533; 2,747,379; 2,912,865; French Nos. 2,355,505; 2,358,159 and 2,375,249; European Patent Office Nos. 4,512 and 2,677; Japanese Nos. 54/063016; 54/073729 and 55/019236 and U.S. Nos. 4,082,735 and 4,082,736. These patents are incorporated herein in full by reference and made a part hereof. The synthesis of n-acetyl-muramyl-L-alanyl-D-isoglutamine can be found in *Biochem. Biophys. Res. Comm.*, 66, 1316 (1975) by C. P. Merser and P. Sinay.

The effective dose of MDP compound will vary depending upon the activity of the particular compound employed and precise figures for each and every MDP compound are not presently known. However, the effective dosage generally will fall in the range of 0.01 mg/kg/dose to 10 mg/kg/dose, preferably between 0.1 and 5 mg/kg/dose. The dosage regime may consist of a single daily dose or b.i.d. or t.i.d. dosing but it is preferred to minimize the number of injections, hence a single dose is most preferred.

The component responsible for enhancing the anti-infective activity of MDP compounds are microscopic vesicles consisting of concentric lipid bilayers, generally spherically shaped, and commonly known as liposomes. Structurally liposomes range in size and shape from long tubes to spheres with dimensions of several hundred angstroms to fractions of a mm. Regardless of the overall shape, the bilayers are generally organized as closed concentric lamellae, with an aqueous layer separating each lamella from its neighbor. The vesicle size mainly ranges between 25 to 30,000 nm diameter and the liquid film between a lamella is about 3 to 10 nm.

Liposomes are most frequently prepared from phospholipids, many of which form lipid bilayer structures spontaneously in aqueous solution, but any molecule having a lipophobic moiety and a hydrophilic moiety, otherwise known as a surfactant, can be used to prepare liposomes. For the purposes of this invention the term "liposome" is intended to cover any concentric lipid bilayer structure consisting of closed concentric lamellae enclosing one or more aqueous-containing compartments and prepared from a pharmaceutically acceptable compound having surfactant properties.

Liposomes can be divided into three categories based on their overall size and the nature of the lamellar structure. To describe these physical classifications, the nomenclature developed at the New York Academy of Sciences meeting on "Liposomes and Their Use in Biology and Medicine," of September 1977 will be used. The three classifications are multilamellar vesicles (MLV), small unilamellar vesicles (SUV) and large unilamellar vesicles (LUV). Small unilamellar vesicles range in diameter from approximately 200 to 500 nm and consist of a single lipid bilayer surrounding an aqueous compartment. A particular characteristic of SUV's is that a large amount about 70%, of the total lipid is located in the outer layer of the vesicle. In addition, the small radius of curvature imposes strain in packing of the lipid molecules resulting in them being rendered metastable in certain circumstances.

Several methods are available for preparing SUV but the most widely used is ultrasonic dispersion either by the immersion of a metal probe directly into a suspension of multilamellar vesicles or the suspension of sealed bio-containing MLV in an ultrasonic cleaning bath. Usually sonication is carried out in an inert atmosphere such as nitrogen or argon to prevent oxidative degradation and hydrolysis of the lipid materials; and usually at a controlled temperature.

The most frequently encountered and easily prepared liposomes are multilamellar vesicles (MLV). Where SUV are single compartmental vesicles of fairly uniform size, MLV vary greatly in size up to 10,000 nm or there about and are multicompartmental in their structure. Preparation is fairly simple and straightforward, and involves dissolving appropriate lipids in an organic solvent which is then evaporated, leaving behind a thin film of dried lipid on the surface of the container. An aqueous solution is then introduced into the container which is swirled by hand to free lipid material from the sides of the container and to disperse lipid aggregates.

Large unilamellar vesicles (LUV) are so named because of their large diameter which ranges from about 600 nm to upwards of 30 microns. Such vesicles may contain one or more bilayers. Several methods are available for preparing LUV, for example slow hydration of a thin layer of lipid with distilled water or an aqueous solution of non-electrolyte will result in the formation of LUV.

A variety of methods for preparing various liposome forms have been described in the periodical literature. A number of patented procedures exist for the preparation of liposomes, all of which may be used in the practice of this invention though it should be noted that, because active ingredient is not being encapsulated, simple straightforward methods for liposome preparation are adequate for the purpose of this invention. Only in those instances where it is necessary to precisely control the type and size of liposome will it be necessary to resort to preparation methods which are more extensive than simply dissolving lipids in an organic solvent, removing the solvent completely and hydrating the lipids with an appropriate MDP compound free solvent.

For the practitioner of this invention who may wish to precisely control the number of layers and vesicle size of the liposomes employed, that person is referred to reviews by Pagano and Weinstein (*Ann. Rev. Biophysic. Bioeng.*, 7, pp. 435–68 (1978)) and Szoka and Papahadjopoulos (*Ann. Rev. Biophysic. Bioeng.*, 9, pp. 467–508 (1980)) and to a number of patents for preparing liposomes such as, for example, U.S. Pat. Nos. 4,229,360; 4,224,179; 4,127,344; 4,193,893; 4,217,344; 4,241,046; 4,078,052 and 4,235,871, all of which are hereby incorporated by reference. Any or all of the liposome-forming procedures described in these patents may be used in preparing liposomes for the practice of this invention. However, it should be understood that preparative methodology in no way limits the scope of this invention as it is the liposome itself which is of importance to this invention, and not how the liposome was realized or prepared.

Furthermore, liposomes prepared with a recognition macromolecule to bind liposomes selectively to a particular cell falls within the scope of this invention. A number of such recognition macromolecules, for example, antibodies, plant lectins, desialylated glycoproteins and the like have been attached to liposomes by non-specific forces whereby one of the macromolecules combining sights. A review of some of the work in this area can be found in the Pagano and Weinstein reference recited above and in, for example U.S. Pat. No. 4,310,505. These materials are incorporated herein by reference and made a part hereof.

Liposomes may be prepared from any surfactant or in combinations of surfactants but, for the practice of this invention, only those surfactants which are pharmaceutically acceptable may be used. That is, useful surfactants should not have or exhibit a deleterious or untoward effect on the host to which they were administered either systemically or at the site of administration.

To form the lamellar phase, a single surfactant material or mixtures can be employed. Surfactants one can use are, for example, ternary or complex lipids, glycerides, cerides, etholides and sterids, namely one of several compounds wherein the hydrophilic group is phosphate, carboxylate, sulfate, amino, hydroxyl and choline group; and the lipophilic group is alkyl or alkylenyl, polyoxyalkylene and an alkyl group substituted with at least one aromatic or cycloalkyl group.

The liposomes may be anionic, basic or neutral depending upon the choice of hydrophilic groups. For instance when a phosphate or a sulfate group is used the resulting liposome will be anionic. When amino-containing surfactants are used the liposomes will have a positive charge, or be cationic liposomes; and when polyethyleneoxy or glycol groups are present in the surfactant, neutral liposomes will be obtained. Compounds suitable for forming liposomes can be found in the following references: *McCutcheon's Detergents and Emulsifiers* and *McCutcheon's Functional Materials*, Allured Pub. Company, Ridgewood, N.J., U.S.A.

Preferred surfactants are phospholipid-related materials such as, for example, lecithin, phosphatidyl ethanolamine, lysolecithin, lysophosphatidylethanolamine, phosphatidylserine, phosphatidyl inositol, sphingomyelin, cephalin, cardiolipin, phosphatidic acid, cerebrosides, dicetyl-phosphate, phosphatidyl-choline and di-palmitoyl-phosphatidylcholine. Additional, non-phosphorous-containing lipids are for instance, stearylamine, dodecylamine, hexadecylamine, cetyl palmitate, glyceryl ricinoleate, hexadecyl stearate, isopropyl myristate, amphoteric acrylic polymers, triethanolamine-lauryl sulphate, alcoyl-aryl sulfonates, polyethoxylated fatty acid amides and the like.

Various additives can be combined with the surfactant so as to modify its permeability characteristics or the superficial charge of said spheres. Representative additives include long chain alcohols and diols; sterols, for example, cholesterol; long chain amines and their quaternary ammonium derivatives; dihydroxyalkylamines; polyoxyethylenated fatty amines; esters of long chain amino alcohols, their salts and quaternary ammonium derivatives; phosphoric esters of fatty alcohols, for example, sodium dicetyl phosphate; alkysulfates, for example, sodium cetyl sulfate; certain polymers such as polypeptides; and proteins.

It should be understood that the surfactant make-up and/or additives used to prepare liposomes may be in any combination or from any natural or synthetic source and so long as the prepared materials are non-toxic and pharmaceutically acceptable.

As a rule of thumb, the amount of liposome material needed to effectively encapsulate a single MDP compound dose will also be adequate to enhance the anti-infective activity of free or unencapsulated MDP. Generally this amount will be between about 0.1 and 1,000 micromoles of surfactant per kg body weight per dose, through it should be understood that there may be instances where more or less liposome-forming material can be used and still realize the enhanced anti-effective response of this invention.

Subject treatment using the methods disclosed herein preferably will be carried out by a parenteral route. Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as pH buffering agents and the like, such as for example, sodium acetate, etc.

As used herein the phrase "serial injection" means that liposomes may be administered first, followed by the MDP compound, or liposome and MDP compound may be injected as a mix (but not encapsulated or associated) and administered simultaneously as one injection, or an MDP compound may be administered followed by liposome material at some appropriate time. Preferably liposomes and MDP compound will be injected within three hours of each other and preferably the liposome material will be injected first followed by administration of the MDP compound. It is more preferred to inject liposomes and MDP compound within one hour of each other. It is most preferable to take prepared liposomes, mix in the MDP compound and administer the mix as a single injection.

EXAMPLE 1

Multilamellar vesicles (MLV's) were formed by drying down egg phosphatidyl choline and brain phosphatidyl serine (7:3 molar ratio) on the inside of a flask. Phosphate-buffered saline lacking divalent cations (PBS) was added (1 mL per 20 micromoles phospholipid), and the flask shaken, either by hand or with a mechanical shaker, until the lipid film was dispersed. When N-acetyl-muramyl-L-alpha-aminobutyrl-D-isoglutamine (abu-MDP) was to be encapsulated, it was included in the aqueous solution before addition to the lipid film. The vesicles formed as the result of shaking the aqueous solution which contained drug were washed to remove unencapsulated drug, pelleted by centrifugation at 30,000 X g, 20–30 min, and then resuspended in PBS. MLV preparations made without drug were either pelleted and resuspended as described, or were used without further treatment.

Mice were injected intravenously with liposomes (4 micromoles phospholipid) and also with free abu-MDP (2–4 mg/kg). The abu-MDP was injected either at the same time as the liposome injection, or 1 hr prior to or 1 hr after the liposome injection. Injections were made at 96 and 48 hr prior to challenge with Candida albicans ($5 \times 10^6$ cells injected intravenously). Control mice were treated with either liposomes only, or abu-MDP only (4 or 60 mg/kg), or abu-MDP (2–4 mg/kg) encapsulated in liposomes, and similarly challenged with Candida albicans. Each treatment group contained 20 mice. All mice were monitored daily for number of survivors. Statistical analysis of survival time was computed using a Mann Whitney U probability analysis, and the numbers of survivors were statistically compared using Fisher Exact probability analysis.

Study results are given in Table I, below. The same protective activity against Candida albicans was obtained whether abu-MDP was encapsulated in MLV, mixed with MLV just prior to treatment, or given 1 hr before or after injection of PBS-containing MLV. P values calculated for survival time and number of survivors, at the time when controls (treated only with MLV or with saline) first reached 100% dead, were all less than 0.03. By comparison, the treatments with the same concentration of abu-MDP alone were ineffective (P greater than 0.05). Only when the concentration of free abu-MDP alone was raised to 60 mg/kg was protective activity obtained equivalent to that seen using the lower dose of abu-MDP (2–4 mg/kg) plus MLV.

TABLE I

Survival of mice treated[a] with abu-MDP either administered before or after, mixed with, or encapsulated in MLV prior to challenge with Candida albicans.

| Compound | abu-MDP dose (mg/kg) | Survival Time (Days) | No. (%) | P values[b] Time | No. | P values[c] Time | No. |
|---|---|---|---|---|---|---|---|
| abu-MDP | 2 | 5.1 | 32 | <0.002 | 0.007 | >0.1 | 1.0 |
| mixed with MLV | 4 | 5.6 | 50 | <0.002 | 0.002 | >0.1 | 0.6 |
| abu-MDP | 2 | 5.1 | 36 | <0.002 | 0.002 | — | — |
| in MLV | 4 | 6.1 | 62 | <0.002 | 0.002 | — | — |
| Saline in MLV | 0 | 3.0 | 0 | —[d] | — | — | — |
| abu-MDP mixed with MLV | 4 | 7.2 | 65 | <0.002 | 0.005 | >0.1 | 0.9 |
| abu-MDP in MLV | 4 | 7.2 | 68 | <0.002 | 0.002 | — | — |
| abu-MDP, then MLV | 4 | 6.7 | 62 | 0.01 | 0.008 | >0.1 | 0.9 |
| MLV, then abu-MDP | 4 | 7.4 | 55 | <0.002 | 0.03 | >0.1 | 0.6 |
| Saline in MLV | 0 | 5.3 | 18 | — | — | — | — |
| abu-MDP | 4 | 4.4 | 0 | NS | NS | — | — |
| abu-MDP | 60 | 6.9 | 45 | 0.01 | 0.05 | — | — |
| Saline | 0 | 3.6 | 0 | — | — | — | — |

[a]Mice received two treatments, at days 4 and 2 before infection.
[b]Comparison was to saline in MLV control, or saline control for groups which did not receive MLV. NS indicates P > 0.05 which was considered not significant.
[c]Comparison was to abu-MDP encapsulated in MLV at same dose level.
[d]Not applicable

EXAMPLE 2

A second experiment was performed by the method described in Example 1, except that the mice were given a single pre-infection treatment at 72 hr prior to challenge, instead of treatments at 96 and 48 hr prior to challenge as was done in Example 1. Results are given in Table II, below. Although the overall protective activity was not as pronounced with one pre-infection treatment, the same conclusion was reached: treating with abu-MDP either mixed with MLV, or administered 1 hr before or after MLV, gave as good protection as when the drug was encapsulated in the MLV (P≦0.05).

TABLE II

Survival of mice treated[a] with abu-MDP either administered before or after, mixed with, or encapsulated in MLV prior to challenge with Candida albicans.

| Compound | abu-MDP dose (mg/kg) | Survival Time (Days) | No. (%) | P values[b] Time | No. | P values[c] Time | No. |
|---|---|---|---|---|---|---|---|
| abu-MDP mixed with MLV | 4 | 6.4 | 30 | 0.01 | NS | >0.1 | 1.0 |
| abu-MDP in MLV | 4 | 6.7 | 35 | 0.002 | 0.02 | — | — |
| abu-MDP, then MLV | 4 | 7.5 | 50 | <0.002 | 0.003 | >0.1 | 0.3 |
| MLV, then abu-MDP | 4 | 7.0 | 50 | <0.002 | 0.003 | >0.1 | 0.3 |
| Saline in MLV | 0 | 4.4 | 5 | —[d] | — | — | — |
| abu-MDP | 4 | 5.2 | 0 | NS | NS | — | — |
| abu-MDP | 60 | 6.4 | 32 | 0.01 | NS | — | — |
| Saline | 0 | 4.9 | 0 | — | — | — | — |

[a]Mice received one treatment, at day 3 before infection.
[b]Comparison was to saline in MLV control, or saline control for groups which did not receive MLV. NS indicates P > 0.05 which was considered not significant.
[c]Comparison was to abu-MDP encapsulated in MDP.
[d]Not applicable

What is claimed is:

1. A method for enhancing the anti-infective activity of a muramyldipeptide (MDP) compound which method comprises serial intravenous injection to an animal in need thereof an anti-infective enhancing amount of unencapsulated MDP compound and liposomes within three hours of each other wherein said MDP compound.

2. The method of claim 1 wherein said liposomes and MDP compound are injected within two hours of each other.

3. The method of claim 1 wherein said MDP compound is N-acetyldesmethylmuramyl-L-alanyl-D-isoglutamine.

4. The method of claim 1 wherein the MDP compound is N-acetylmuramyl-L-alanyl-D-isoglutamine.

5. The method of claim 1 wherein the MDP compound is N-acetyldesmethylmuramyl-L-alpha-aminobutyryl-D-isoglutamine.

6. The method of claim 1 wherein said MDP compound is N-acetylmuramyl-L-alpha-aminobutyryl-D-isoglutamine.

7. The method of claim 1 wherein said MDP compound is N-acetylmuramyl-L-valyl-D-isoglutamine.

8. The method of claim 1 wherein said MDP compound is N-acetylmuramyl-L-threonyl-D-isoglutamine.

9. The method of claim 1 wherein said MDP compound is N-acetylmuramyl-L-seryl-D-isoglutamine.

* * * * *